(12) United States Patent
Jung et al.

(10) Patent No.: US 6,480,002 B1
(45) Date of Patent: Nov. 12, 2002

(54) BATTERY INSPECTION SYSTEM

(75) Inventors: Jae-Hyun Jung, Anyang (KR); Kwang-Jun Yoon, Seoul (KR); Hyeong-Cheol Kim, Seongnam (KR); Yong-Won Kim, Suwon (KR); Won Choi, Suwon (KR); Hyoung-Jo Jeon, Yongin (KR); Hyun-Kwon Jung, Kwangmyong (KR)

(73) Assignee: Samsung Electronics Co., Ltd., Suwon (KR)

( * ) Notice: Subject to any disclaimer, the term of this patent is extended or adjusted under 35 U.S.C. 154(b) by 0 days.

(21) Appl. No.: 09/966,364

(22) Filed: Oct. 1, 2001

(30) Foreign Application Priority Data

May 7, 2001 (KR) .............................................. 01-24671

(51) Int. Cl.$^7$ .......................... G01N 27/416; G06K 9/00
(52) U.S. Cl. ........................................ 324/425; 382/141
(58) Field of Search .......................... 320/165; 324/425; 429/90; 414/281–286; 340/572.1, 572.4, 572.8; 382/141

(56) References Cited

FOREIGN PATENT DOCUMENTS

KR        20-0159115        7/1999

*Primary Examiner*—Gregory J. Toatley, Jr.
(74) *Attorney, Agent, or Firm*—Staas & Halsey LLP (57) ABSTRACT

Disclosed herein is a battery inspection system. The battery inspection system includes a battery feeding conveyor for feeding batteries to be inspected. One or more transfer robots are positioned near the rear end of the battery feeding conveyor for transferring batteries fed through the battery feeding conveyor to inspection and discharge positions. An X-ray generator is positioned under the transfer robots for applying X-rays to batteries transferred by the transfer robots. A satisfactory battery discharging conveyor is positioned near the transfer robots for discharging satisfactory battery moved by the transfer robots and having been inspected. A defective battery discharging robot is positioned near the front end of the satisfactory battery discharging conveyor for removing defective batteries from batteries moving along the satisfactory battery discharging conveyor and having been inspected.

7 Claims, 9 Drawing Sheets

BATTERY INSPECTION SYSTEM

BACKGROUND OF THE INVENTION

1. Field of the Invention

The present invention relates generally to a battery inspection system that is used to automatically inspect batteries such as lithium batteries using X-rays.

2. Description of the Prior Art

In general, lithium batteries can be fabricated to be relatively thin, and thus mounted on electronic apparatuses while occupying relatively small spaces, so the lithium batteries are widely employed for a variety of electronic apparatuses, such as imaging devices, communications equipments, optical instruments, medical instruments, computers, mobile phones and the like.

A general lithium battery is comprised of a square-shaped can made of metal, such as stainless steel, and a jelly roll wound in the form of a roll in the metallic can. After the jelly roll is placed in the metallic can and thereby the assembly of the lithium battery is completed, the lithium battery undergoes inspection for detecting manufacturing defects. The battery inspection system of the present invention is a system for inspecting lithium batteries for incorrect positioning of jelly rolls contained within metallic cans. In more detail, the battery inspection system of the present invention inspects the lithium batteries whether the winding of jelly rolls in metallic cans is corrected or not, the spacing between jelly rolls and metallic cans is maintained within an allowable error range or not, there is any infiltration of impurities into the metallic cans during assembly or not, or the like, using X-rays.

Figure 1:
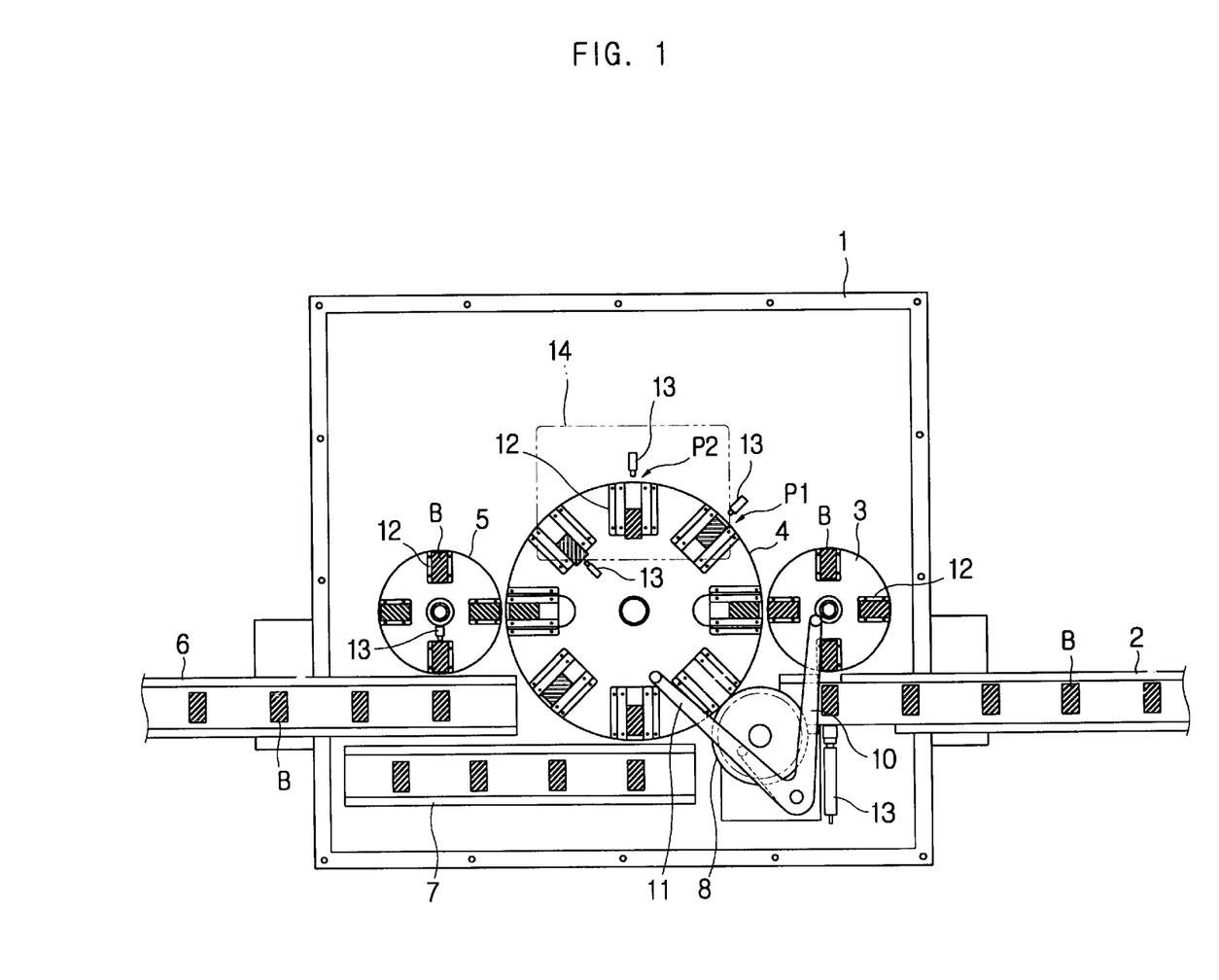
FIG. 1 is a plan view schematically illustrating a conventional battery inspection system.

FIG. 1 is a plan view schematically showing a conventional battery inspection system. The conventional battery inspection system is comprised of a flat inspection table 1, a battery feeding conveyor 2, a circular feeding plate 3, a circular inspection plate 4, a circular discharging plate 5, a satisfactory battery discharging conveyor 6, a defective battery discharging conveyor 7, and a cam 8. The three circular plates 3, 4 and 5 and the cam 8 are rotatably positioned on the inspection table 1. The rear end of the battery feeding conveyor 2 is situated near the circular feeding plate 3, the front end of the satisfactory battery discharging conveyor 6 is situated near the circular discharging plate 5, and the front end of the defective battery discharging conveyor 7 is situated near the circular inspection plate 4.

A pair of bars 10 and 11 are attached to the cam 8 to be rotated by the rotation of the cam 8 within a predetermined range of angles.

Four battery accommodating members 12 are formed on the circular feeding plate 3, four battery accommodating members 12 are formed on the circular discharging plate 5, and eight battery accommodating members 12 are formed on the circular inspection plate 4. In order to arrange batteries B accommodated and moved in the battery accommodating members 12 at a precise inspection position or to move batteries B to the next circular plate or the conveyor, a plurality of cylinders 13 are positioned around the circular plates 3, 4 and 5. An X-ray generator 14 is situated under the circular inspection plate 4 to inspect batteries B.

In the inspection of batteries by the conventional battery inspection system, batteries B fed by the battery feeding conveyor 2 are removed to the battery accommodating members 12 by the cylinder 13 and, thereafter, the circular feeding plate 3 is rotated. At the same time, while the cam 8 is rotated, the bar 10 pushes the battery B positioned on the circular feeding plate 3 to the battery accommodating member 12 of the circular inspection plate 4. While the circular inspection plate 4 is sequentially rotated at regular intervals, the battery B removed to the circular inspection plate 3 is first arranged by the cylinder 13 to be situated at a first inspection position P1, and exposed to X-rays generated by the X-ray generator 14 to be inspected for defects at a position P2. Thereafter, the battery B is arranged at a second inspection position P2 by the cylinder 13, and another side of the battery B is inspected for defects. Subsequently, a satisfactory battery is removed to the circular discharging plate 5 by the cylinder 13, while a defective battery is further rotated at a predetermined angle and sent to the defective battery discharging conveyor 7 by the bar 11 attached to the cam 8. The satisfactory battery removed to the circular discharging plate 5 is sent to the satisfactory battery discharging conveyor 6 by the cylinder 13 and transferred to the next process.

With the repetition of the above-described process, the batteries fed through the battery feeding conveyor 2 are automatically inspected for defects.

However, in the conventional battery inspection system, since batteries are moved or arranged by a plurality of cylinders and bars, the jelly rolls may deviate from their correct positions by the shock of impacts exerted by the cylinders or bars in the process of inspecting jelly rolls and metallic cans for defects, thereby causing satisfactory batteries to become defective batteries.

In addition, in the conventional battery inspection system, its battery accommodating members are formed to accommodate only specifically sized batteries and the stroke lengths of its cylinders and bars are adjusted to remove the specifically sized batteries to the next process or arrange them at an appropriate inspection position. Hence, in order to inspect different models of differently sized batteries for defects, the size of the accommodating space of the battery accommodating members and the positions of the cylinders and the bars should be adjusted to fit the size of the differently sized batteries. As a result, excessive time is required to adjust the size of the accommodating space of the battery accommodating members and the positions of the cylinders and the bars to fit the size of the differently sized batteries, so the productivity of the batteries is deteriorated by the conventional battery inspection system.

SUMMARY OF THE INVENTION

Accordingly, the present invention has been made keeping in mind the above problems occurring in the prior art, and an object of the present invention is to provide a battery inspection system, which is capable of inspecting batteries for defects without causing the relative positions of their jelly rolls and metallic cans to be undesirably varied.

Another object of the present invention is to provide a battery inspection system, which is capable of being rapidly and conveniently adjusted for inspecting different models of type batteries.

In order to accomplish the above object, the present invention provides a battery inspection system, comprising: a battery feeding conveyor for feeding batteries to be inspected; one or more transfer robots positioned near the rear end of the battery feeding conveyor for transferring batteries fed through the battery feeding conveyor to inspection and discharge positions; an X-ray generator positioned under the transfer robots for applying X-rays to batteries transferred by the transfer robots; a satisfactory battery discharging conveyor positioned near the transfer robots for discharging satisfactory batteries moved by the transfer robots and having been inspected; and a defective battery discharging robot positioned near the front end of the satisfactory battery discharging conveyor for removing defective batteries from batteries moving along the satisfactory battery discharging conveyor and having been inspected.

The battery inspection system may further comprise a control unit for determining whether batteries are defective on the basis of X-ray images generated by the X-ray generator and controlling the defective battery discharging robot.

The control unit may comprise an image multiplier tube for multiplying X-ray images transmitted from the X-ray generator into visible ray images, a camera for photographing the images of the image multiplier tube, and a control panel for interpreting photographs taken by the camera and determining whether batteries are defective.

The battery inspection system may further comprise a defective battery discharging conveyor positioned near the front end of the satisfactory battery discharging conveyor for discharging defective batteries removed by the defective battery discharging robot.

The transfer robots may be comprised of a vertical transfer robot for simultaneously picking up batteries to be inspected and having been inspected and a horizontal transfer robot positioned under the vertical transfer robot for transferring batteries transferred by the vertical transfer robot to a precise inspection position, the X-ray generator may be positioned under the horizontal transfer robot, so that the vertical transfer robot simultaneously picks up batteries to be inspected and having been inspected from the battery feeding conveyor and the horizontal transfer robot, and transfers the batteries to the horizontal transfer robot and the satisfactory battery discharging conveyor, respectively, and the horizontal transfer robot positions batteries transferred by the vertical transfer robot right over the X-ray generator.

Preferably, The image multiplier tube and the camera are positioned over the horizontal transfer robot.

The battery inspection system may further comprise a battery separating conveyor positioned at the rear end of the battery feeding conveyor for separating a number of batteries equal in number to the number of batteries to be transferred by each of the transfer robots from the batteries fed through the battery feeding conveyor.

BRIEF DESCRIPTION OF THE DRAWINGS

The above and other objects, features and other advantages of the present invention will be more clearly understood from the following detailed description taken in conjunction with the accompanying drawings, in which.

DESCRIPTION OF THE PREFERRED EMBODIMENTS

Hereinafter, the construction and operation of a battery inspection system in accordance with the present invention is described in detail with reference to accompanying drawings. Since the construction of a lithium battery, which is a kind of battery comprised of a metallic can and a jelly roll inserted therein, is well known, the description of the construction of the lithium battery is omitted in this specification.

Figure 2:
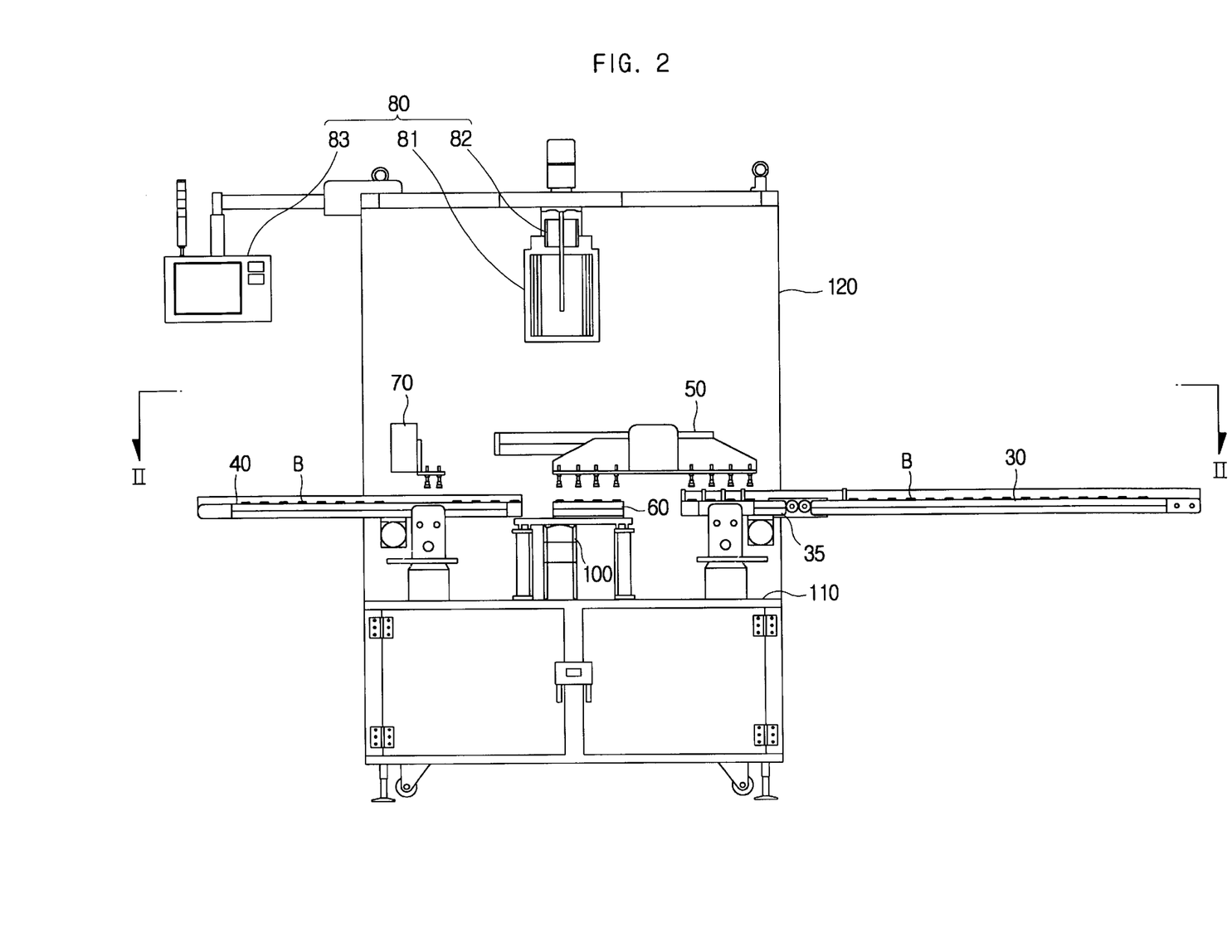
FIG. 2 is a front view showing a battery inspection system in accordance with the present invention.
Figure 3:
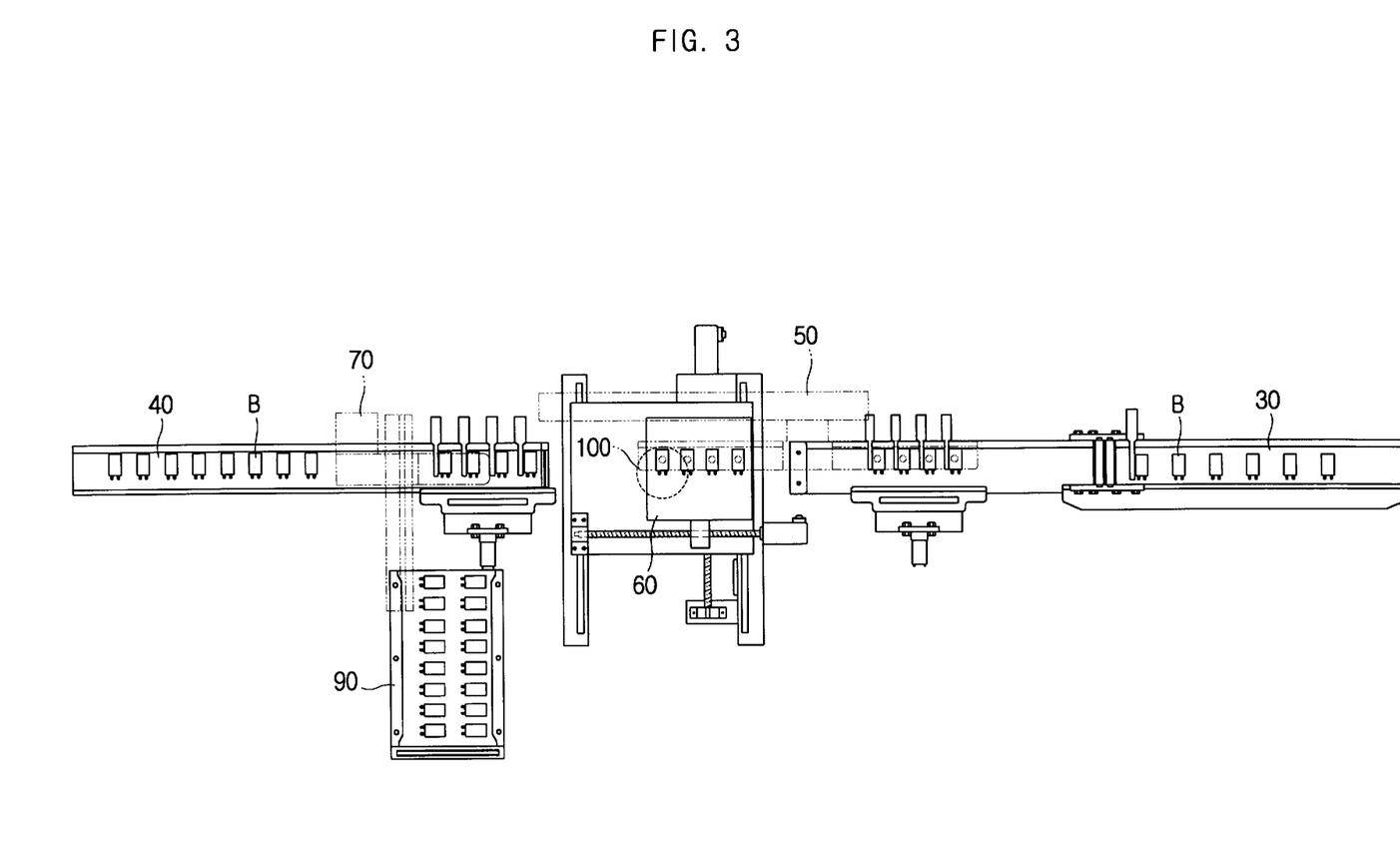
FIG. 3 is a plan view taken along line II—II of FIG. 2.

FIGS. 2 and 3 are front and plan views showing the arrangement of the component parts of the battery inspection system of the present invention, respectively. As illustrated in the drawings, the battery inspection system of the present invention is comprised of a battery feeding conveyor 30 for feeding batteries B to be inspected, a satisfactory battery discharging conveyor 40 for discharging satisfactory batteries B having been inspected, vertical and horizontal transfer robots 50 and 60 positioned between the conveyors 30 and 40 to transfer batteries B to inspection and discharge positions, a defective battery discharging robot 70 for removing defective batteries B from the satisfactory battery discharging conveyor 40, a control unit 80 for inspecting the batteries B and determining whether the batteries B are defective, a defective battery discharging conveyor 90 for collecting and discharging defective batteries B removed from the defective battery discharging robot 70, and an X-ray generator 100 for applying X-rays to batteries B.

The X-ray generator 100 and the horizontal transfer robot 60 are positioned on an inspection table 110, and the vertical transfer robot 50 is positioned over the horizontal transfer robot 60. The control unit 80 is comprised of an image multiplier tube 81 for multiplying X-ray images transmitted from the X-ray generator 100 into visible ray images, a camera 82 for photographing the visible ray images multiplied by the image multiplier tube 81, and a control panel 83 for interpreting photographs taken by the camera 82 and determining whether the batteries B are defective. The image multiplier tube 81 and the camera 82 are integrated into a single body, aligned with the X-ray generator 100, and positioned over the vertical transfer robot 50.

A battery separating conveyor 35 is positioned between the battery feeding conveyor 30 and the horizontal transfer robot 60 to separate a proper number of batteries B for one time examination from the batteries B fed to the battery separating conveyor 35 and to supply the separated batteries B.

In order to prevent X-rays generated by the X-ray generator 100 from being discharged to the outside, the inspection table 110, the three robots 50, 60 and 70, the image multiplier tube 91, the camera 82, the battery separating conveyor 35, the defective battery discharging conveyor 90, and the front portion of the satisfactory battery discharging conveyor 40 are shielded from the outside by a shielding wall 120. The control panel 83 is situated outside of the shielding wall 120 so as to allow an operator to approach and manipulate the control panel 83.

Hereinafter, the construction and operation of the component parts of the battery inspection system in accordance with the present invention are separately described.

Figure 4:
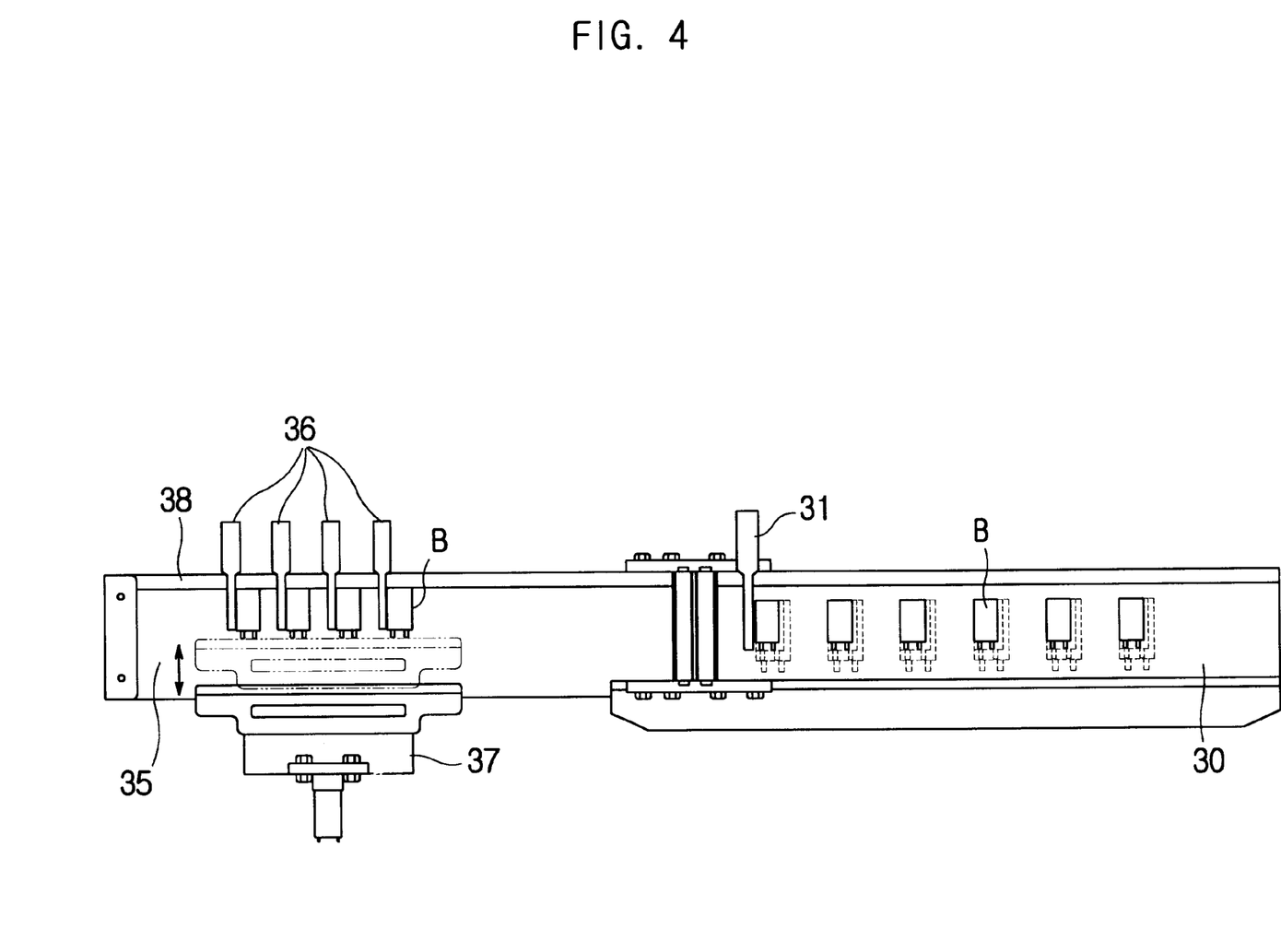
FIG. 4 is a schematic plan view showing the battery feeding conveyor and the battery separating conveyor of FIG. 2.

FIG. 4 is a view showing the battery feeding conveyor 30 and the battery separating conveyor 35 for feeding batteries through the shielding wall 120. Assembled batteries B are fed into the interior of the inspection system along the battery feeding conveyor 30 and the battery separating conveyor 35 to be inspected by the battery inspection system. The battery feeding conveyor 30 and the battery separating conveyor 35 are arranged to be somewhat spaced apart from and aligned with each other. A stopper 31 is mounted on the rear portion of the battery feeding conveyor 35, and stops batteries B from being fed after a predetermined number of batteries B (in this embodiment, the vertical robot 50 is adapted to transfer four batteries, so the predetermined number is four) are conveyed to the battery separating conveyor 35 until the next inspection is initiated.

Four stoppers 36 are mounted on the battery separating conveyor 35 while being spaced apart from each other. A moving rail 37 is positioned on the lower side of the battery separating conveyor 35, while a stationary rail 38 is positioned on the upper side of the battery separating conveyor 35.

Four batteries B transferred from the battery feeding conveyor 30 to the battery separating conveyor 35 by the above-described construction are located at predetermined positions in a line, and, thereafter, pushed toward the stationary rail 38 by the moving rail 37 so as to be arranged to be precisely gripped by the vertical transfer robot 50.

In accordance with the present invention, the battery inspection system is designed to be adapted to inspect different models of batteries each model having a dfferent size. In FIG. 4, different models of batteries are illustrated in dotted lines. Additionally, in order to inspect the different models of batteries, the stroke length of the moving rail 37 mounted on the battery separating conveyor 35 can be adjusted through the control panel 83 of the control unit 80.

After the batteries B disposed on the battery separating conveyor 35 are transferred by the vertical transfer robot 50, the stopper 31 mounted on the battery feeding conveyor 30 is lifted up so that another four batteries are conveyed to the battery separating conveyor 35.

The battery feeding conveyor 30 and the battery separating conveyor 35 convey batteries by repeating the above-described operation.

Figure 5:
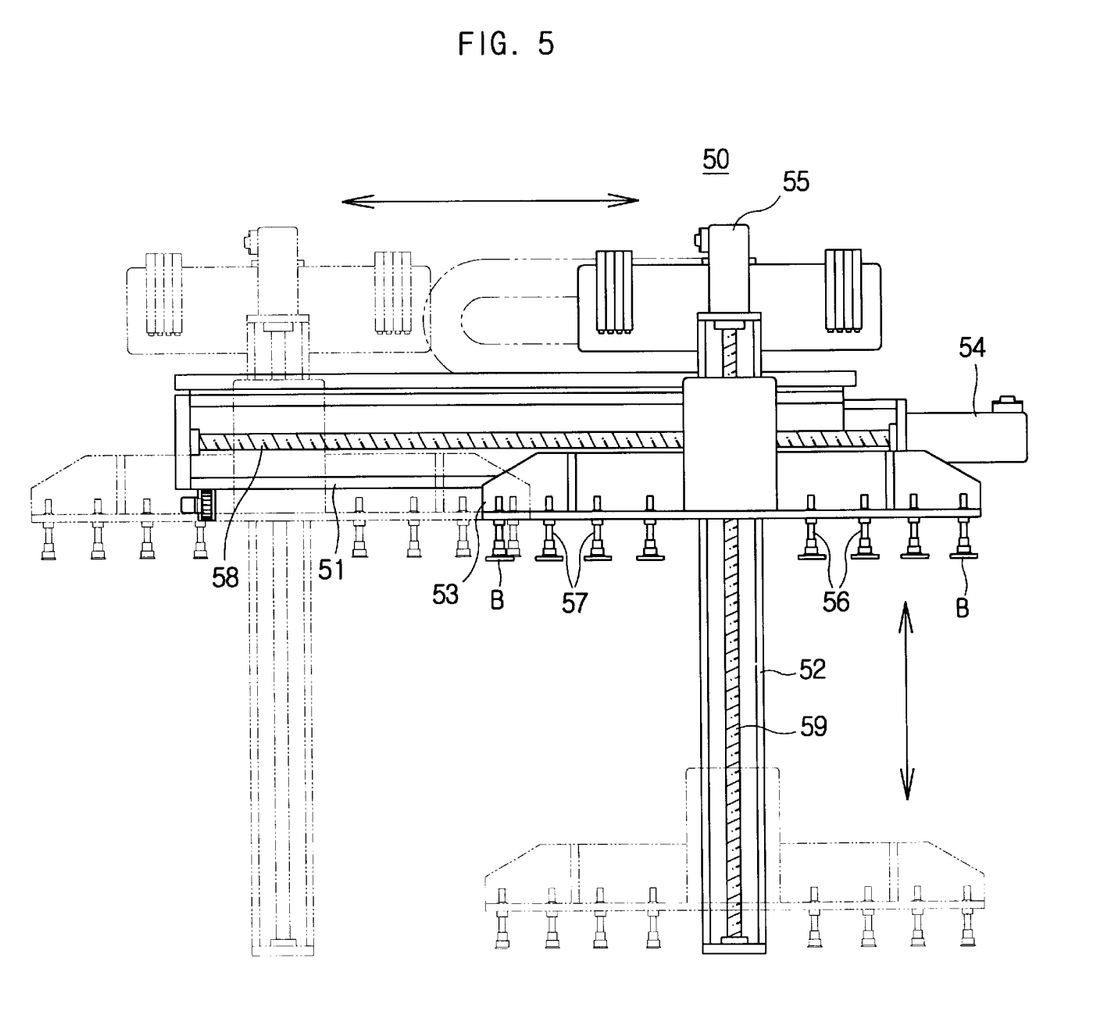
FIG. 5 is a schematic front view showing the vertical transfer robot of FIG. 2.

FIG. 5 is a view showing the construction of the vertical transfer robot 50. The vertical transfer robot 50 carries out the operation of simultaneously picking up four batteries B to be inspected from the battery separating conveyor 35 and four batteries B having been inspected from the horizontal transfer robot 60, and transferring the two groups of batteries B to the horizontal transfer robot 60 and the satisfactory battery discharging conveyor 40, respectively. In order to carry out such an operation, the vertical transfer robot 50 includes a stationary horizontal rail 51, a vertical rail 52 attached to be moved along the horizontal rail 51, and a battery transfer member 53 attached to be moved along the vertical rail 53. The horizontal and vertical rails 51 and 52 each have a motor 54 or 55 and a screw 58 or 59. Accordingly, the vertical rail 52 attached to the screw 58 of the horizontal rail 51 by a nut (not shown) is horizontally moved along the vertical rail 51 by rotating the screw 58 by the operation of the motor 54. In a similar manner, the battery transfer member 53 attached to the screw 59 of the vertical rail 52 by a nut (not shown) is vertically moved along the vertical rail 52 by rotating the screw 59 by the operation of the motor 55.

Four battery feeding pads 56 for removing batteries to be inspected from battery separating conveyor 35 to the horizontal transfer robot 60 and four battery discharging pads 57 for removing batteries having been inspected from the horizontal transfer robot 60 to the satisfactory battery discharge conveyor 40 are located beside the battery transfer member 53, respectively. The pads 56 and 57 are operated in such a way that the pads 56 and 57 remove batteries B by sucking batteries B using a vacuum and, thereafter, separate the batteries B from the pads 56 and 57 by equalizing the pressure of the pads 56 and 57 with the ambient pressure.

In the operation of the vertical transfer robot 50, the battery transfer member 53 is lowered down along the vertical rail 52 by a predetermined vertical distance, attaches four batteries to be inspected to the battery feeding pads 56 from battery separating conveyor 35 and another four batteries having been inspected to the battery discharging pads 57 from the horizontal transfer robot 60, and is lifted up along the vertical rail 52. Thereafter, the vertical rail 52 is horizontally (in FIG. 5, to the left) moved along the horizontal rail 51 by a predetermined distance, and the battery transfer member 53 is lowered down along the vertical rail 52 to remove to the horizontal transfer robot 60 the batteries attached to the battery feeding pads 56 and, at the same time, remove to the satisfactory battery discharging conveyor 40 the batteries attached to the battery discharging pads 57. Thereafter, the battery transfer member 53 is vertically lifted up along the vertical rail 52, and the vertical rail 52 is horizontally moved to its original position along the horizontal rail 51 and stands by to transfer batteries to be inspected and having been inspected. Such movement of the vertical rail 52 and the battery transfer member 53 is illustrated as two-dot chain lines.

Figure 6:
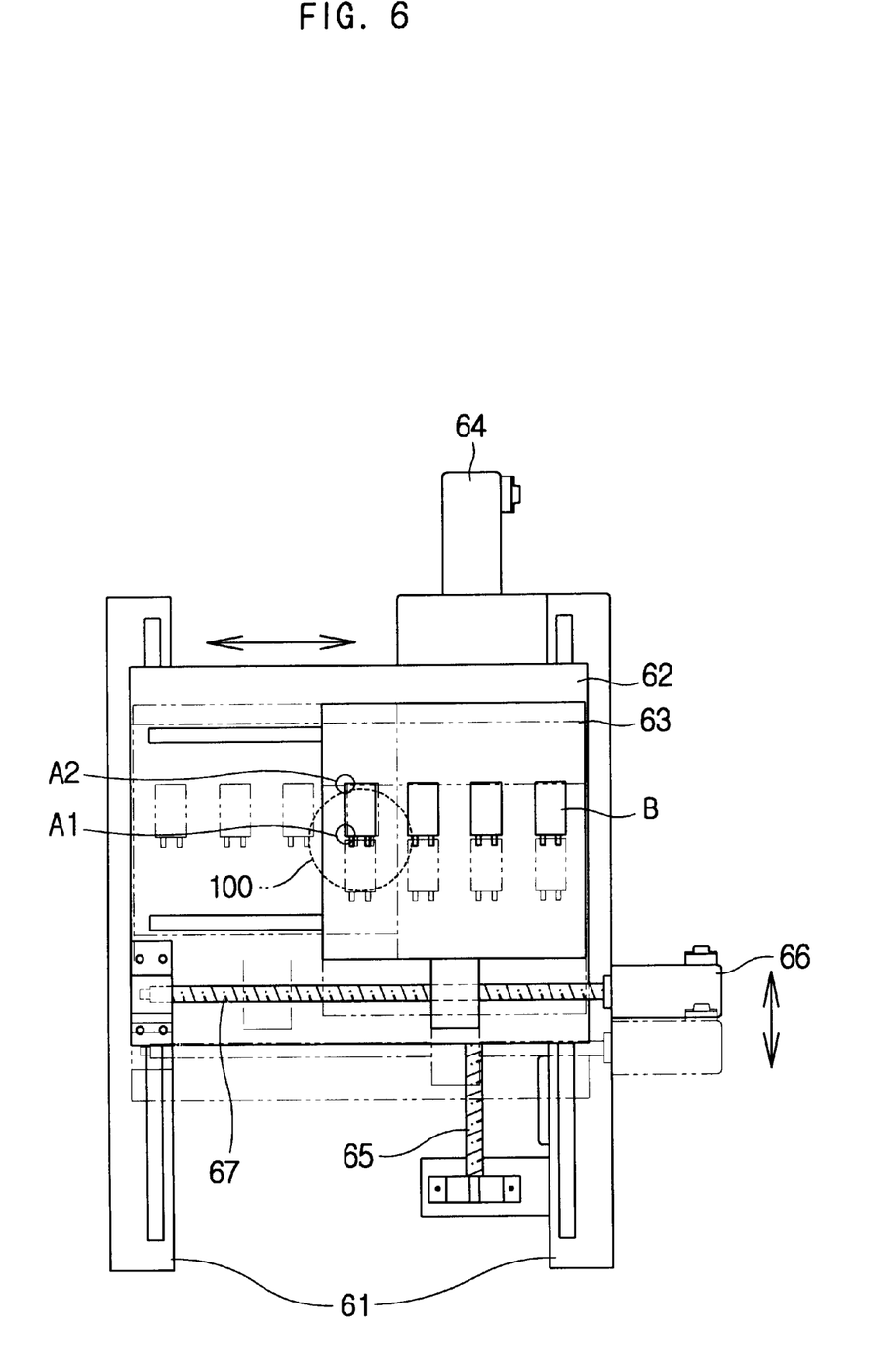
FIG. 6 is a schematic plan view showing the horizontal transfer robot of FIG. 2.

FIG. 6 is a view showing the construction of the horizontal transfer robot 60. The horizontal transfer robot 60 serves to precisely and sequentially position four batteries transferred by the vertical transfer robot 50 at the X-ray applying position of the X-ray generator 100. In order to carry out such an operation, the horizontal transfer robot 60 is comprised of a pair of guiders 61 spaced apart from each other by a predetermined distance and vertically arranged, a vertical moving plate 62 attached to the guiders 61 to be vertically movable, and a horizontal moving plate 63 attached to the vertical moving plate to be horizontally movable. The guiders 61 are provided with a motor 64 for moving the vertical moving plate 62 and a screw 65 to be rotated by the operation of the motor 64, and, in the same manner, the horizontal moving plate 63 is provided with a motor 66 and a screw 67. Batteries B are laid down on the top of the horizontal moving plate 63 and moved to the X-ray applying position of the X-ray generator 100 by the horizontal moving plate 63.

In the operation of the vertical transfer robot 60 constructed as described above, when four batteries B are transferred by the vertical transfer robot 50 and laid down on the horizontal moving plate 63, the vertical moving plate 62 is moved to arrange the batteries B to coincide with the position of the X-ray generator 100. Thereafter, in order to apply X-rays to the first inspection portion A1 of the battery positioned nearest to the X-ray generator 100, the horizontal moving plate 63 is moved to cause the first inspection portion A1 to coincide with the center of the X-ray generator 100, the X-ray generator 100 applies X-rays to the first inspection portion A1 and the image is transmitted to the image multiplier tube 81 of the control unit 80. Thereafter, the vertical moving plate 63 is moved to cause the second inspection portion A2 to coincide with the center of the X-ray generator 100, the X-ray generator 100 applies X-rays to the second inspection portion A2 and the image is transmitted to the image multiplier tube 81 of the control unit 80. After X-rays are applied to the two inspection portions A1 and A2 of the first battery, whether the first battery is defective is determined by the control panel 83, and simultaneously a second battery begins to be inspected in the same manner to determine whether the second battery is defective.

When the inspection of the four batteries is completed through the process described above, the batteries having been inspected are transferred to the satisfactory battery discharging conveyor 40 by the vertical transfer robot 50 and, at the same time, another four batteries are laid down on the vertical moving plate 63 to be inspected.

Figure 8:
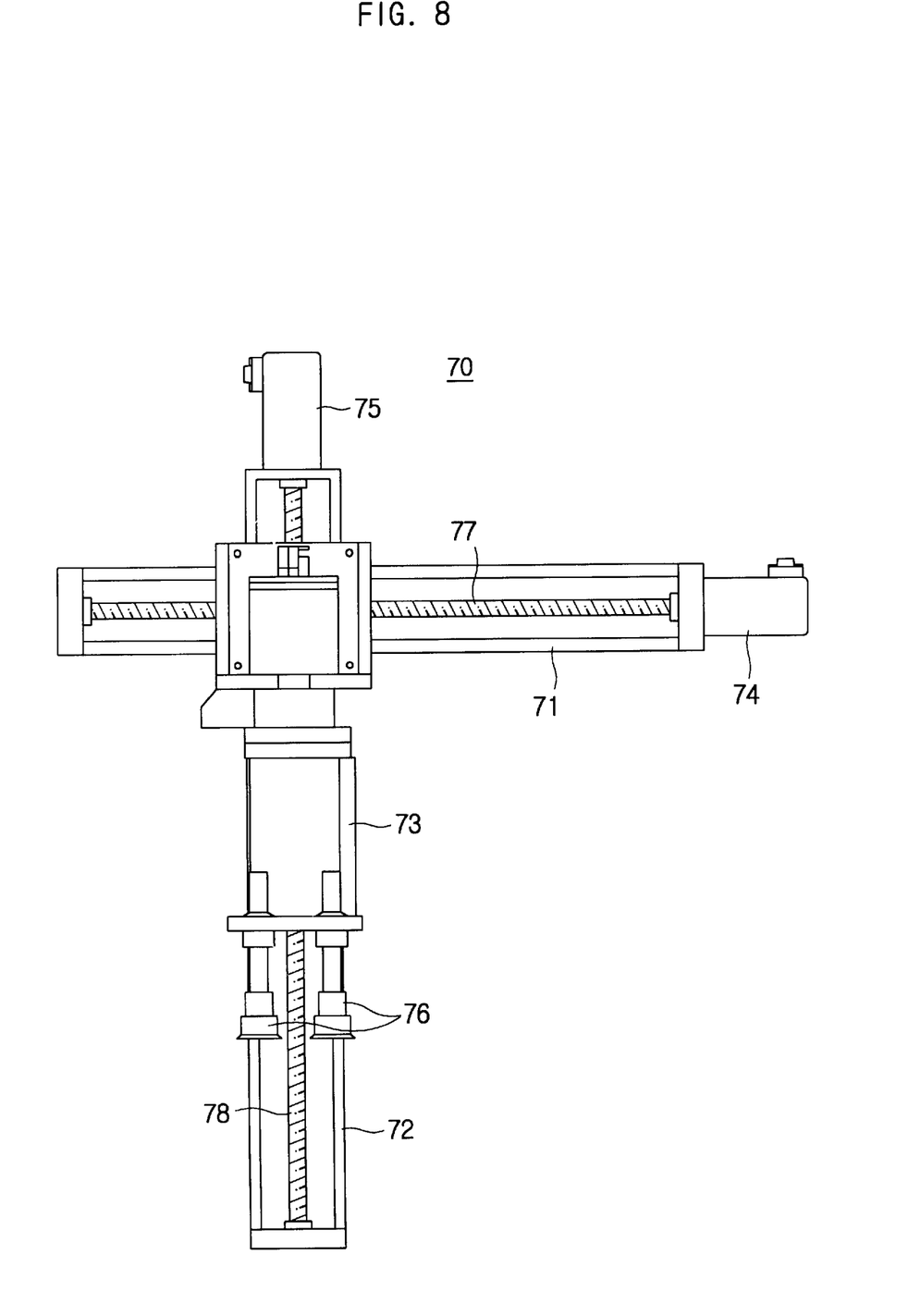
FIG. 8 is a schematic front view showing the defective battery discharging robot of FIG. 2.
Figure 9:
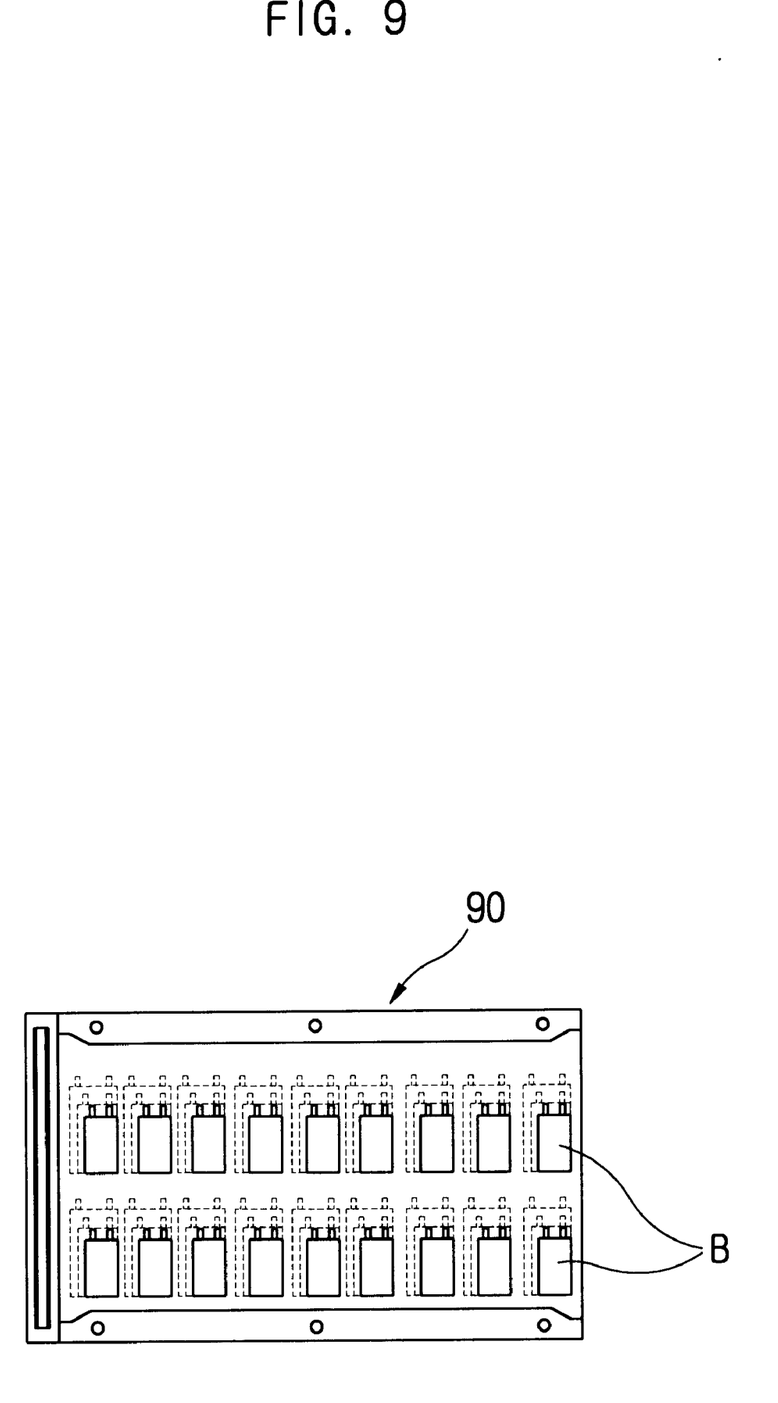
FIG. 9 is a schematic plan view showing the defective battery discharging conveyor of FIG. 3.

Batteries determined to be defective by the control unit 80, as described above, are transferred to the satisfactory battery discharging conveyor 40 by the vertical transfer robot 50, and a defective battery discharging robot 70 is positioned on the front portion of the satisfactory battery discharging conveyor 40 to remove defective batteries. This operation is described with reference to FIG. 2 showing the construction of the battery inspection system, FIG. 7 showing the satisfactory battery discharging conveyor 40, FIG. 8 showing the defective battery discharging robot 70, and FIG. 9 showing the defective battery discharging conveyor 90.

As shown in FIG. 2, the defective battery discharging robot 70 is positioned over the front portion of the satisfactory battery discharging conveyor 40 that is aligned with the battery feeding conveyor 30 and positioned in the vicinity of the horizontal transfer robot 60, and a defective battery discharging conveyor 90 is positioned to cross the front portion of the satisfactory battery discharging conveyor 40.

Figure 7:
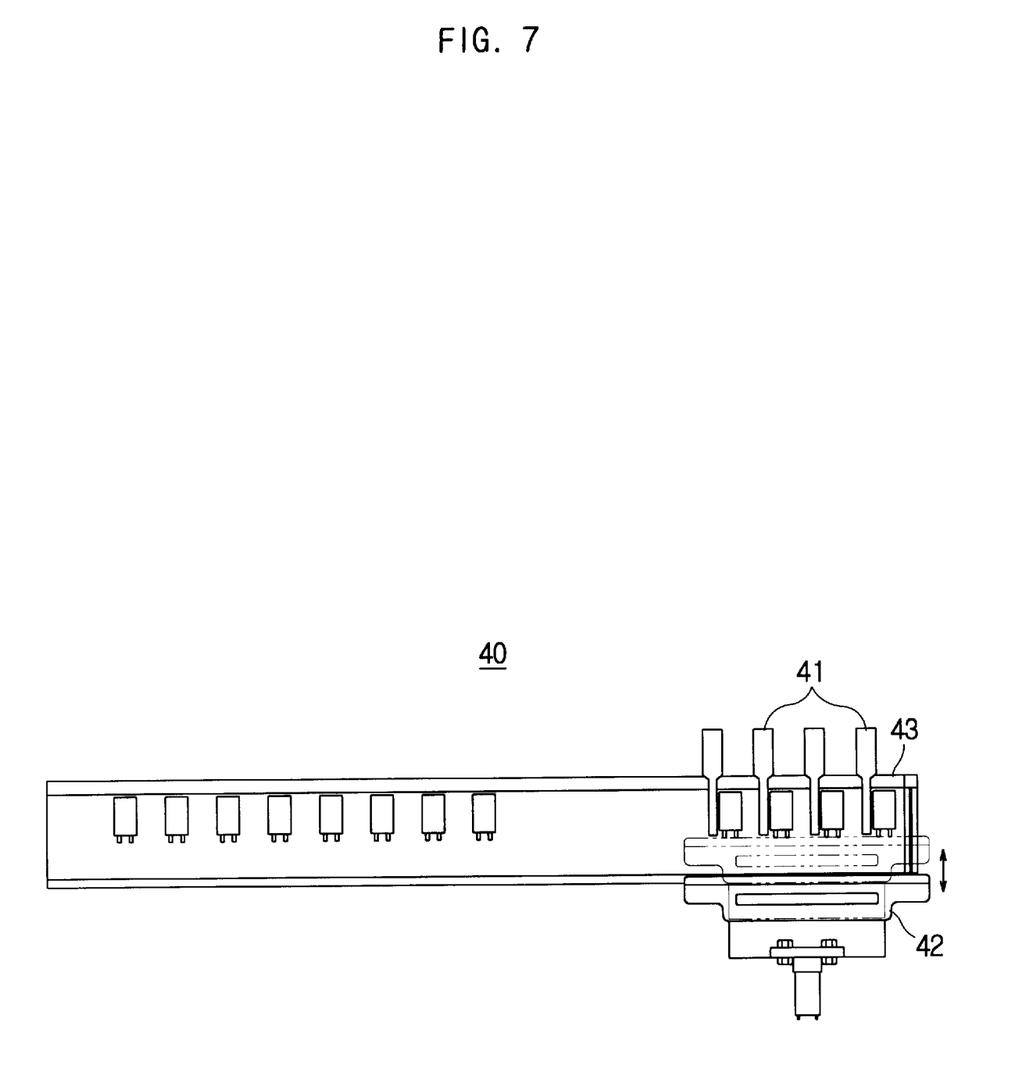
FIG. 7 is a schematic plan view showing the satisfactory battery discharging conveyor of FIG. 2.

As shown in FIG. 7, four stoppers 41 are mounted on the front portion of the satisfactory battery discharging conveyor 40 to be vertically movable, and serve to prevent batteries B from being moved along the satisfactory battery discharging conveyor 40 after four batteries having been inspected are laid down on the satisfactory battery discharging conveyor 40 until defective batteries are removed by the defective battery discharging conveyor 90. A moving rail 42 is positioned on the lower side of the satisfactory battery discharging conveyor 40 and a stationary rail 43 is positioned on the upper side of the satisfactory battery discharging conveyor 40, so batteries B having been inspected are pushed to the stationary rail 43 by the moving rail 42.

In this case, the inspection system can be rapidly and conveniently adapted for different models of are type batteries by adjusting the stroke distance of the moving rail 42.

As shown in FIG. 8, the defective battery discharging robot 70 is similar to the vertical transfer robot 50 in construction except that the number of pads for removing defective batteries is two. That is, the defective battery discharging robot 70 is comprised of a stationary horizontal rail 71, a vertical rail 72 attached to be horizontally movable along the horizontal rail 71, and a battery transfer member 73 attached to be vertically movable. The horizontal and vertical rails 71 and 72 each have a motor 74 or 75 and a screw 77 or 78 rotated by the motor 74 or 75. Accordingly, the vertical rail 72 attached to the screw 77 of the horizontal rail 71 by a nut (not shown) is horizontally moved along the vertical rail 71 by rotating the screw 77 by the operation of the motor 74. In a similar manner, the battery transfer member 73 attached to the screw 78 of the horizontal rail 72 by a nut (not shown) is vertically moved along the vertical rail 72 by rotating the screw 78 by the operation of the motor 75. The battery transfer member 73 is provided with two battery discharging pads 76 to remove defective batteries from batteries B, which have been inspected and are laid down on the satisfactory battery discharging conveyor 40.

As depicted in FIG. 9, the defective battery discharging conveyor 90 discharges defective batteries B transferred by the defective battery discharging robot 70 while being loaded with defective batteries B arranged in two rows. The dotted lines of the drawing indicate different models of batteries.

In the operation of the defective battery discharging robot 70, when four batteries having been inspected are transferred to the satisfactory battery discharging conveyor 40 by the vertical transfer robot 50, the batteries are prevented from being moved by the stoppers 41 and simultaneously the moving rail 42 is moved to the stationary rail 43 to arrange the batteries. Thereafter, the battery transfer robot 73 of the defective battery discharging robot 70 is lowered down along the vertical rail 72 and picks up batteries using the pair of battery discharging pads 76. If one battery is defective, one battery discharging pad 76 is operated; if two batteries are defective, two battery discharging pads 76 are operated at the same time. Thereafter, the battery transfer member 73 is lifted up, and the vertical rail 72 is moved along the horizontal rail 71 and lays down defective batteries on the defective battery discharging conveyor 90. Thereafter, the defective battery discharging robot 70 is returned to its original position so as to remove other defective batteries.

As a result, batteries are inspected for defects, and only satisfactory batteries are transferred to the next process by a series of operations of the battery inspection system as described above.

As described above in detail, the present invention provides a battery inspection system in which the transfer of batteries to an inspection position or a discharge position is carried out by robots provided with vacuum suction pads, thereby preventing the batteries from being deformed and stably inspecting the batteries.

In addition, when it is necessary to inspect different models of batteries the simple adjustment of the moving positions of robots suffices for the inspection of the batteries, thereby allowing the inspection system to be rapidly and conveniently adapted for the inspection of the different models of batteries.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A battery inspection system, comprising:
   a battery feeding conveyor for feeding batteries to be inspected;
   one or more transfer robots positioned near the rear end of said battery feeding conveyor for transferring batteries fed through the battery feeding conveyor to inspection and discharge positions;
   an X-ray generator positioned under said transfer robots for applying X-rays to batteries transferred by said transfer robots;
   a satisfactory battery discharging conveyor positioned near said transfer robots for discharging satisfactory batteries moved by said transfer robots and having been inspected; and
   a defective battery discharging robot positioned near the front end of said satisfactory battery discharging conveyor for removing defective batteries from batteries moving along said satisfactory battery discharging conveyor and having been inspected.

2. The battery inspection system according to claim 1, further comprising a control unit for determining whether batteries are defective on the basis of X-ray images generated by said X-ray generator and controlling said defective battery discharging robot.

3. The battery inspection system according to claim 2, wherein said control unit comprises an image multiplier tube for multiplying X-ray images transmitted from the X-ray generator into visible ray images, a camera for photographing the images of the image multiplier tube, and a control panel for interpreting photographs taken by the camera and determining whether batteries are defective.

4. The battery inspection system according to claim 1, further comprising a defective battery discharging conveyor positioned near the front end of the satisfactory battery discharging conveyor for discharging defective batteries removed by the defective battery discharging robot.

5. The battery inspection system according to claim 1, wherein:

said transfer robots are comprised of a vertical transfer robot for simultaneously picking up batteries to be inspected and having been inspected and a horizontal transfer robot positioned under the vertical transfer robot for transferring batteries transferred by the vertical transfer robot to a precise inspection position;

said X-ray generator is positioned under the horizontal transfer robot;

said vertical transfer robot simultaneously picks up batteries to be inspected and having been inspected from the battery feeding conveyor and the horizontal transfer robot, and transfers the batteries to the horizontal transfer robot and the satisfactory battery discharging conveyor, respectively; and said horizontal transfer robot positions batteries transferred by the vertical transfer robot right over the X-ray generator.

6. The battery inspection system according to claim 5, wherein said image multiplier tube and said camera are positioned over the horizontal transfer robot.

7. The battery inspection system according to claim 1, further comprising a battery separating conveyor positioned at the rear end of said battery feeding conveyor for separating a number of batteries equal in number to the number of batteries to be transferred by each of the transfer robots from the batteries fed through said battery feeding conveyor.

* * * * *